US012017086B1

United States Patent
Mok

(10) Patent No.: US 12,017,086 B1
(45) Date of Patent: Jun. 25, 2024

(54) APPARATUS AND METHODS FOR A SLEEP DISORDER TREATMENT

(71) Applicant: Allure Medical Spa PLLC, Shelby Township, MI (US)

(72) Inventor: Charles Mok, Shelby Township, MI (US)

(*) Notice: Subject to any disclaimer, the term of this patent is extended or adjusted under 35 U.S.C. 154(b) by 0 days.

(21) Appl. No.: 18/231,664

(22) Filed: Aug. 8, 2023

(51) Int. Cl.
*A61N 5/06* (2006.01)
*A61N 5/067* (2006.01)
*G16H 50/20* (2018.01)

(52) U.S. Cl.
CPC ......... *A61N 5/0603* (2013.01); *A61N 5/0625* (2013.01); *A61N 5/067* (2021.08); *G16H 50/20* (2018.01); *A61N 2005/0604* (2013.01); *A61N 2005/0606* (2013.01); *A61N 2005/0628* (2013.01)

(58) Field of Classification Search
CPC .... A61N 5/0603; A61N 5/0625; A61N 5/067; A61N 2005/0604; A61N 2005/0606; A61N 2005/0628; A61N 5/06–2005/073; G16H 5/20; G16H 50/00–50/80; A61B 18/20–18/28; A61B 5/72–5/7296
See application file for complete search history.

(56) References Cited

U.S. PATENT DOCUMENTS

| | | | | |
|---|---|---|---|---|
| 2005/0278002 | A1* | 12/2005 | Eimerl | A61B 18/203 607/88 |
| 2007/0265606 | A1* | 11/2007 | DeBenedictis | A61B 18/20 606/15 |
| 2018/0310892 | A1* | 11/2018 | Perschbacher | A61B 5/002 |
| 2021/0322784 | A1* | 10/2021 | Shuter | A61N 5/0616 |

OTHER PUBLICATIONS

Shiffman, Harvey S., Jay Khorsandi, and Nichole M. Cauwels. "Minimally invasive combined Nd: YAG and Er: YAG laser-assisted uvulopalatoplasty for treatment of obstructive sleep apnea." Photobiomodulation, Photomedicine, and Laser Surgery 39.8 (2021): 550-557. https://doi.org/10.1089/photob.2020.4947 (Year: 2021).*
Fotana, LightWalker brochure, https://www.fotona.com/media/documents/dentistry/brochures/96008_lw_brochure.pdf; accessed Oct. 31, 2023 (Year: 2023).*

* cited by examiner

Primary Examiner — Jonathan T Kuo
(74) Attorney, Agent, or Firm — Caldwell Intellectual Property Law

(57) ABSTRACT

An apparatus and method for a sleep disorder treatment including an input device a light-emitting device for use in precise tissue heating and tightening, including one or more light settings, a processor; and a memory communicatively connected to the processor, the memory containing instructions configuring the processor to receive user data from the input device, receive diagnostic test data from a plurality of diagnostic tests, wherein a diagnostic test comprises a nocturnal polysomnography test, generate a plurality of light emission parameters for the one or more light settings as a function of the user data and treat user with the light-emitting device in oral tissue area.

20 Claims, 8 Drawing Sheets

APPARATUS AND METHODS FOR A SLEEP DISORDER TREATMENT

FIELD OF THE INVENTION

The present invention generally relates to the field of lasers. In particular, the present invention is directed an apparatus and method for a sleep disorder treatment.

BACKGROUND

It is estimated that 50 to 70 million adults in the U.S. are affected by a sleep disorder and over 25 million adults have obstructive sleep apnea. Sleep is a basic human need and is critical to both physical and mental health. Sleep disorders are linked to various physical and emotional problems and can contribute to or exacerbate mental health conditions. There are currently very few effective treatments for sleep disorders, including sleep apnea.

SUMMARY OF THE DISCLOSURE

In an aspect, an apparatus for a sleep disorder treatment including an input device, a light-emitting device, including one or more light settings, a processor, and a memory communicatively connected to the processor, the memory containing instructions configuring the processor to receive user data from the input device, receive diagnostic test data from a plurality of diagnostic tests, wherein the diagnostic test includes a nocturnal polysomnography test, generate a plurality of light emission parameters for the one or more light settings as a function of the user data and treat a user with the light-emitting device in oral tissue area.

In another aspect, a method for a sleep disorder treatment including a light-emitting device and receiving, by the processor, a user data from the input device, receiving, by the processor, diagnostic test data from a plurality of diagnostic tests, wherein the diagnostic test includes a nocturnal polysomnography test, generating, by the processor, a plurality of light emission parameters for the one or more light settings as a function of the user data and treating a user with the light-emitting device in oral tissue area.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and method for sleep disorder treatment utilizing precise tissue destruction using a light-emitting device such as a laser and can be used to help users who suffer from sleep apnea. The light-emitting device may decrease the amplitude of snoring and the effects of sleep apnea by means of a gentle, laser-induced tightening effect caused by the heating of oral mucosa tissue.

Figure 1:
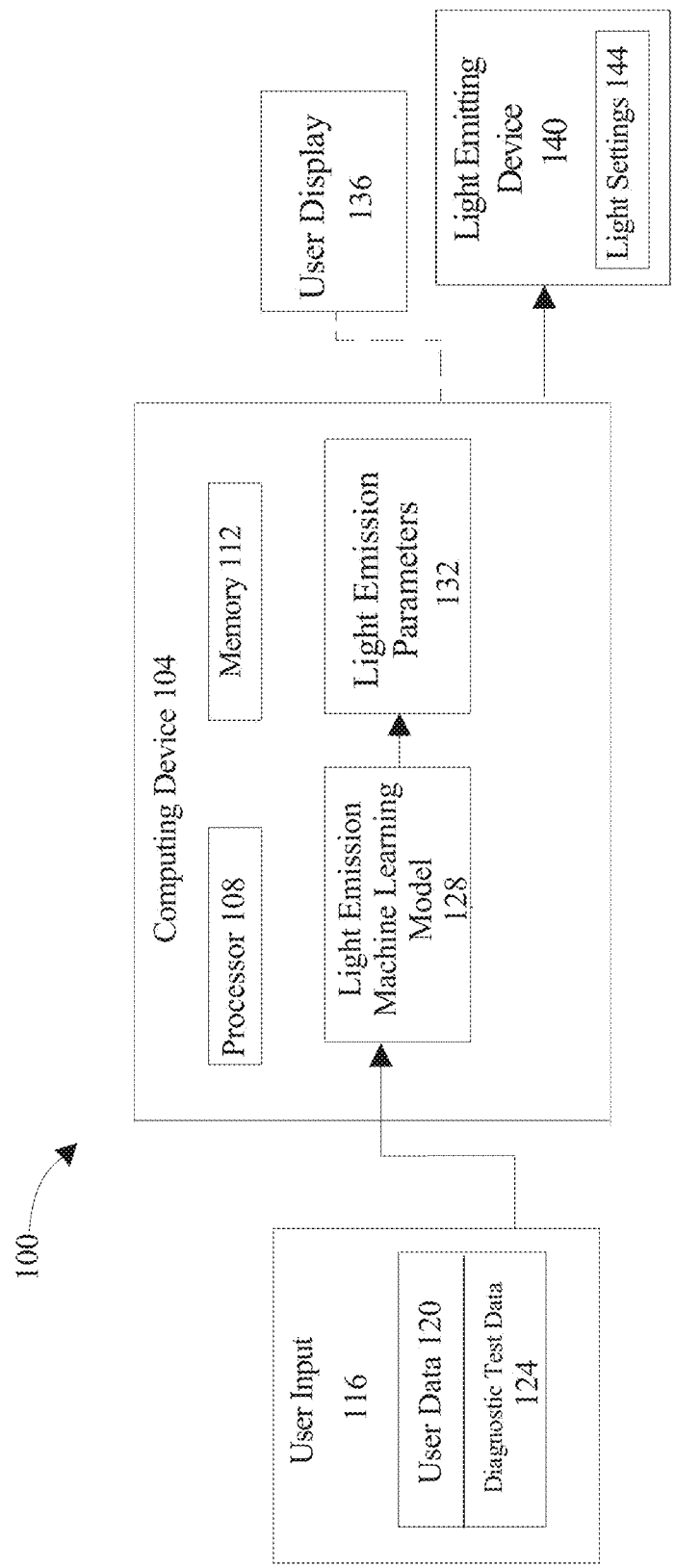
FIG. 1 is a block diagram of an exemplary embodiment of an apparatus for a sleep disorder treatment.

Referring now to FIG. 1, an exemplary embodiment of an apparatus 100 for a sleep disorder treatment is illustrated. "Sleep disorder" as used in this disclosure may be defined as a problem with the quality, timing and amount of sleep in a person. There are various types of sleep disorder such as obstructive sleep apnea, insomnia, narcolepsy, restless leg syndrome and the like. "Obstructive sleep apnea" as used in this disclosure is defined as a sleep disorder in which breathing stops and starts due to throat muscles which relax and block the flow of air into the lungs. There may be a resistance of airflow during sleep due to partial or complete collapse of the upper airway mainly the oropharyngeal tract and it may occur due to failure of the muscle to keep the airway open or that supports the soft tissue in the throat such as tongue and soft palate. The most common symptoms during sleep are snoring, choking at night, nocturia, and insomnia. Chronicity of sleep apnea affects the function of different organs and systems most importantly the brain and cardiovascular system thereby altering the body metabolic balance.

Referring now to FIG. 1, apparatus 100 may include, be included in, and/or be a computing device 104. Computing device 104 may be designed and/or configured to perform any method, method step, or sequence of method steps in any embodiment described in this disclosure, in any order and with any degree of repetition. For instance, a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Apparatus 100 also includes a processor 108. Processor 108 may include any processor incorporated in any computing device as described in this disclosure, including without limitation a microcontroller, microprocessor, digital signal processor (DSP) and/or system on a chip (SoC) as described in this disclosure. Processor and/or computing device may include, be included in, and/or communicate with a mobile device such as a mobile telephone or smartphone. A computing device incorporating processor 108 may include a single computing device operating independently, or may include two or more computing device operating in concert, in parallel, sequentially or the like; two or more computing devices may be included together in a single computing device or in two or more computing devices. Processor 108 and/or computing device may interface or communicate with one or more additional devices as described below in further detail via a network interface device. Network interface device may be utilized for connecting processor 108 and/or computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A computing device including processor 108 may include but is not limited to, for example, a computing device or cluster of computing devices in a first location and a second computing device or cluster of computing devices in a second location. A computing device including processor 108 may include one or more computing devices dedicated to data storage, security, distribution of traffic for load balancing, and the like. A computing device including processor 108 may distribute one or more computing tasks as described below across a plurality of computing devices of computing device, which may operate in parallel, in series, redundantly, or in any other manner used for distribution of tasks or memory between computing devices. A computing device including processor 108 may be implemented using a "shared nothing" architecture in which data is cached at the worker, in an embodiment, this may enable scalability of apparatus 100 and/or computing device.

With continued reference to FIG. 1, processor 108 and/or computing device may be designed and/or configured to perform any method, method step, or sequence of method steps in any embodiment described in this disclosure, in any order and with any degree of repetition. For instance, processor 108 and/or computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 108 and/or computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to reference FIG. 1, apparatus 100 includes a memory 112, which may be implemented in any manner suitable for a primary and/or secondary memory described in this disclosure. Memory 112 may include instructions configuring processor 108 to perform various tasks. In some embodiments, apparatus 100 may include a computing device 104, where computing device includes processor 108 and/or memory 112. Memory 112 may be communicatively connected to processor 108. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, apparatus 100 is configured to receive a user input 116 which may include an input device. "Input device," as used in this disclosure refers a device that is configured to receive input from a user. For example, data input device may refer to a user generated input method or a may refer to a computer-generated input method. Examples of data input device include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device may further include a plurality of sensors. Input device may further include a photoelectric sensor having three color filters corresponding to the red, green, and blue color space. The photoelectric sensor outputs data in the form of voltages corresponding to a color. A "photoelectric sensor" as used in this disclosure is defined as a device used to determine the distance, absence, or presence of an object by using a light transmitter, often infrared, and a photoelectric receiver. A photoelectric sensor consists primarily of an emitter for emitting light and a receiver for receiving light. When emitted light is interrupted or reflected by the sensing object, it may change the amount of light that arrives at the receiver. The receiver may then detect this change and convert it to an electrical output. For example, the photoelectric sensor may sense that a user is within the proximity of the sensor.[[* ₿ Additionally, or alternatively, data input device may include a video capture device. The video capture device may record still or moving images and transmit the images to the computing device. As described below, the computing device may then determine objects and colors within the still or moving images using machine learning algorithms. In some embodiments, apparatus 100 may receive user input 116 from one or more external computing devices. An "external computing device" as used in this disclosure is defined as any a computing device that is distinct from apparatus 100 and/or computing device. An external computing device may include any computing device as described in this disclosure. A "user input", as used in this disclosure, is a form of data entry received from an individual and/or group of individuals, such as an individual and/or group of individuals that is using and/or interacting with apparatus 100. User input 116 may include, but is not limited to, user data 120. "User data" as used in this disclosure is defined as information related to the patient intake process such as patient clinical data, payment plan information, Health Insurance Portability and Accountability Act (HIPAA) agreement data and the like. Apparatus 100 may be configured to receive the plurality of user input 116 and user data 120. For instance, as described above, the plurality of user data 120 may include, but is not limited to, user's skin datum, tissue datum, collagen datum and the like. "Skin datum" as used in this disclosure is defined as a datum regarding the state of user's skin. For example, skin datum may include data regarding user's skin thickness, skin lesions and the like. "Tissue datum" as used in this disclosure is defined as a datum regarding a group of cells that have a similar structure and that function together as a unit. For example, tissue datum may include data regarding a user's skin, mucosa, and the like. The plurality of user data 120 may also include tissue surface datum. "Tissue surface datum" as used in this disclosure is defined as datum regarding a thin layer or sheet of cells that cover the outside of the body. For example, the organs, international passageways that lead to the exterior of the body and the lining of the moveable joint cavities. By way of another example, tissue surface datum may include data regarding a user's skin, pericardium, abdominal cavities, intramuscular tissue and the like. "Collagen datum" as used in this disclosure is defined as a datum regarding the state of a user's collagen. For example, a user with a level of collagen datum may present with wrinkles, joint pain and the like. The plurality of user data 120 may also include a boundary datum. "Boundary datum" as used in this disclosure is defined as a predetermined area for a user to guide the laser device. For example, a boundary datum may be a predetermined area of the throat of a patient who suffers from obstructive sleep apnea.

Still referring to FIG. 1, user input 116 may include but is not limited to diagnostic test data 124 from a plurality of diagnostic tests. "Diagnostic test data" as used in this disclosure is defined as information resulting from a diagnostic test that a patient has received. In some embodiments, the plurality of tests may be conducted to gain comprehensive understanding of patient's health and customize individual treatment. "Diagnostic test" as used in this disclosure, is defined as a medical procedure performed to detect, diagnose, or monitor a medical condition, medical condition processes, susceptibility or to determine a course of treatment. As a non-limiting example, the plurality of tests (e.g., medical tests) may include a nocturnal polysomnography test. A "nocturnal polysomnography test" is defined as a test to detect sleep apnea which includes being hooked up to equipment that monitors heart, lung and brain activity, breathing patterns, arm and leg movements, and blood oxygen levels while a user is asleep. A plurality of tests (e.g., medical tests) may also include a complete blood count (CBC) test, kidney test, liver test, thyroid panel, urinalysis, lipid panel and the like. In some embodiments, the plurality of tests may include autoimmune test. In an embodiment, the diagnostic test data 124 may include blood count test data. "Blood count test data" as used in this disclosure is defined as data from a blood test used to evaluate your overall health and detect a wide range of disorders, including anemia, infection, leukemia and the like 3An "autoimmune test" as used in this disclosure is defined as a test that screens for antinuclear antibodies, which are a category of antibodies that attach the healthy proteins within the cell nucleus. The autoimmune test may include an antinuclear antibody test (ANA) which is one of the first tests that are typically used when a patient may be showing symptoms of an autoimmune disorder. As a further non-limiting example, an autoimmune test may include gastrointestinal (GI) effect test, celiac panel, thyroid panel, cortisol urine test, diurnal cortisol test and the like. In some embodiments, the plurality of tests may include toxicology panel. As a non-limiting example, the toxicology panel may include stool test, drug test, serum toxicology test, hair follicle test and the like. In some embodiments, the plurality of tests may include genetic testing. In some embodiments, the plurality of tests may include examining the patient's previous prescriptions, current prescriptions, family medical history, nutraceutical intake, and the like. In an embodiment, processor 108 may obtain patient information from a hospital database, an application programming interface and the like.

Continuing in reference to FIG. 1, apparatus 100 may include a light-emitting device 140 for use in precise tissue destruction by heating and tightening. Light-emitting device 140 may include one or more light settings 144. "Light settings" as used in this disclosure is defined as a setting of the beam of intense light emitted by the device. "Light-emitting device" as used in this disclosure is defined as a laser device that emits a light capable of tissue destruction and tightening. For example, a light-emitting device may include a Er:YAG laser. The word "laser" is an acronym for light amplification by stimulated emission of radiation. For example, a laser may emit light through a process of optical amplification based on the stimulated emission of electromagnetic radiation. "Er:YAG (erbium-doped yttrium aluminum garnet) laser" as used in this disclosure is defined as a solid a state laser whose active laser medium is erbium-doped yttrium aluminum garnet and typically emits infrared light. "Tissue destruction and tightening," as used in this disclosure, is the process of tissue destruction and tissue tightening through the use of a light-emitting device. For example, use of infrared light radiation to heat the collagen within the skin wherein certain frequencies of this radiation may cause changes to the outer layers of collagen and stimulate the production of new collagen, as a result, this may cause the skin to appear tighter. Due to age, a skin's collagen begins to break down and tissues start to relax, this relaxed tissue in the back of the throat is typically what causes the snoring sound, (when someone breathes while sleeping), utilizing a laser that targets the water in the skin's collagen in the uvula and back of the throat may result in heating this tissue and may cause some immediate contraction of the tissue, which may result in less snoring, improve sleep apnea and other sleeping disorders. For example, the light-emitting device 140 may utilize heat which may be absorbed by the collagen fibers and gently damaged them which in turn may draw the immune system's attention to the area and the body's natural processes may begin to heal and rebuild the collagen in the damaged areas, this may make the tissue stronger and may result in tightening and strengthening of the loose tissues in the back of the throat. This process may be repeated until desired result is achieved.

Still referencing FIG. 1, light-emitting device 140 may include a laser such as a ruby laser system, diode laser system, argon laser, carbon dioxide laser, neodymium-doped yttrium aluminum garnet laser systems and the like. A "ruby laser system" as used in this disclosure is defined as a solid-state laser that uses a synthetic ruby crystal as the laser medium. The active laser medium (laser gain/amplification medium) may be a synthetic ruby rod that is energized through optical pumping (typically by a xenon flashtube). Light-emitting device 140 may include a diode laser system. A "diode laser system" as used in this disclosure is defined as a laser which may use semiconductor technology that produces coherent projection of light in the visible to infrared range. Light-emitting device 140 may include a neodymium-doped yttrium aluminum garnet (Nd:YAG) laser system. A "neodymium-doped yttrium aluminium garnet (Nd:YAG) laser" as used in this disclosure is defined as a synthetic crystal and medium used in high-powered solid-state lasers via photo disruption. Light-emitting device 140 may also include an argon laser. "Argon laser" as used in this disclosure is defined as a laser that emits light especially in the blue and green regions of the visible spectrum, operates by means of a high-voltage current through ionized argon gas, and may be utilized in laser surgery. Light-emitting device 140 may include a carbon dioxide ($CO_2$) laser. A "carbon dioxide laser" as used in this disclosure is defined as a powerful infrared laser based on a gas mixture in which light is amplified by excited carbon dioxide molecules. Light-emitting device 140 may also include non-laser intense pulsed light ("IPL") devices. "Non-laser intense pulsed light device," as used in this disclosure, is defined as a device which is capable of high output bursts of a broad spectrum of light. For example, the light-emitting device may use a Xenon flash lamp to destroy specific tissue while leaving surrounding tissue undamaged. Light-emitting device 140 may be able to produce varying wavelengths of light ranging from 400 nanometers to 1200 nanometers.

Still referring to FIG. 1, light-emitting device 140 may include one or more optical elements for focusing, collimating, and/or transmitting light emitted by light source. One or more optical elements may include a focal optical suite, which may bend light to converge to a real and/or virtual focal point. Focal optical suite may be reflective, diffractive, adaptive, and/or refractive; for instance, and without limitation, focal optical suite may include two or more lenses spaced apart, where spacing between lenses may be varied to modify a focal length of transmitted light. Dispersal and/or focus of transmitted light may be controlled using electronically focused lens and/or reflective assembly, where adjustment of distances or alignment between lenses and/or mirrors may be electrically or mechanically actuated. Intensity or temporal composition of transmitted light may be variable as well, where variation may be modified using varied voltage levels, electrical current levels, waveforms, multiple pulses, duty cycles, pulse widths, passive or active optical elements, such as Q-switches, acoustical optical tunable filters (AOTF), acousto-optical modulators, electro-optical modulators, and/or spatial light modulators (SLM). Electrical voltage and current levels, and durations to light source may be regulated analog or digitally by output of a logic circuit and/or processor to a digital to analog converter, an on/off cycle to a transistor such as a power field-effect transistor, pulse width modulation provided natively by a processor, or the like.

Still in reference to FIG. 1, light-emitting device 140 may include at least one light setting 144. At least one light setting 144 may include a power density setting. "Power density" as used in this disclosure refers to the given number of photons directed to a concentrated area. The power density setting is calculated as a function of a power and a spot size of the light-emitting device. Power of the light-emitting device is power that is delivered through the light emitted from the light-emitting device. Spot size refers to the area in which the light is delivered. Spot size may be quantified in square centimeters. Power density setting may be quantified in joules per square centimeter. For example, power density with a larger output setting may be achieved by either increasing the power output or decreasing the spot size. Power density setting with a larger output may be desired in situations where more photons would be needed for a desired target. Power density setting may range from 5,000 kJ to 50,0000 kJ for example. The power density setting may be calculated by a dial on the light-emitting device 140. Power density setting may also be calculated by the computing device which is described in more detail below. The data correlating to a specific power density setting may be quantified as power density datum.

Still referring to FIG. 1, one or more light settings 144 of light-emitting device 140 may also include a wavelength setting. "Wavelength setting" as used in this disclosure is defined as the wavelength of light that may be produced by the light-emitting device. The wavelength setting may be quantified in nanometers. Wavelength may be important in precise tissue destruction (heating) as the wavelength may determine the chromophore that should be targeted by the light. For example, due to the combination of high degree of penetration in skin and absorption by respiratory chain components, light in the spectral range from 600 to 1300 nm may be useful for promoting wound healing, tissue repair, and skin rejuvenation. Wavelength setting of light-emitting device 140 may range from 400 nanometers to 12000 nanometers. Wavelength setting of the light-emitting device 140 may be controlled through a dial or through input device as described above. The wavelength setting may also be controlled by the computing device as described in further detail below. The data correlating to a specific wavelength setting may be quantified as wavelength datum.

Still referring to FIG. 1, one or more light settings 144 of light-emitting device 140 may also contain a pulse width setting. A "pulse width" (sometimes also known as "pulse length") as defined in this disclosure is the exposure time of the light-emitting device 140 on the surface of a patient's skin. Pulse width is quantified in seconds. The duration of the pulse width may be dependent on the thickness of user's tissue/skin. For example, a patient with a thinner skin/tissue would require a smaller pulse width as the thinner tissue may heat up quickly, whereas a patient with thicker tissue/skin would require a higher pulse width as thicker tissue/skin takes longer to heart up. Pulse width for tissue/skin destruction/heating may range from between 2 milliseconds up to 40 milliseconds. Pulse width setting may be used to increase or decrease the pulse width in the light-emitting device 140. The data correlating to a specific pulse width setting may be quantified as a pulse width datum Still referring to FIG. 1, one or more light settings 144 of light-emitting device 140 may include a cooling setting. "Cooling setting" as defined in this disclosure is any form of cooling that may occur to reduce the temperature on a surface. For example, light-emitting device 140 may contain a fan configured to blow air onto the heated surface, which may be an area of user's skin, thereby dissipating any heat. Furthermore, the light-emitting device 140 may use air conditioned or cryogenic air as a method to cool the heated surface as a function of a cooling setting. The dissipation of heat from the surface of patient's skin may aid in minimization of burns and other damages that occur to the skin due to the light-emitting device 140. Cooling setting may be controlled through a dial, push button or input device described above. Cooling setting may also be controlled by the computing device described below. The data correlating to a specific cooling setting may be quantified as cooling datum.

Still in reference to FIG. 1, light-emitting device 140 may include a handle so that the user can properly grip the light-emitting device 140 in their hand. Light-emitting device 140 may further include a push button located on a surface of the light-emitting device 140. The pressing of the push button may activate or focus the light that is emitted from the light-emitting device 140. For example, processor may receive a signal when the push button device is pressed, and the processor 104 may be configured to activate the light emitted from the light-emitting device 140 in response.

Still referring to FIG. 1, apparatus 100 may be configured to utilize a light emission machine learning model 128 to generate the plurality of light emission parameters 132. Plurality of light emission parameters 132 may then be transmitted to light-emitting device 140 or to a user display 136. A "user display" as used in this disclosure is defined as a device with a screen which shows rendered electronic images. For example, a user display may include a computer monitor, phone screen, television, and the like. Apparatus 100 may be configured to output a plurality of light emission parameters 132 by analyzing the plurality of user input 116 using a light emission machine learning model 128 trained by a light emission training data. "Plurality of light emission parameters" as used in this disclosure are defined as the data corresponding to the one or more light settings on a light-emitting device. In some embodiments the plurality of light emission parameters 132 may include the power density datum, the wavelength datum, the pulse width datum, the cooling datum, repetition datum, and the like. "Repetition datum" as defined in this disclosure is data referring to required repetitions for proper tissue destruction/heating by light-emitting device 140. For example, a user may need to guide light-emitting device 140 over the throat area three times before the tissue/skin is properly destroyed. A "machine-learning model," as used in this disclosure, is a mathematical and/or algorithmic representation of a relationship between inputs and outputs, as generated using any machine-learning process including without limitation any process as described above and stored in memory, an input is submitted to a machine-learning model once created, which generates an output based on the relationship that was derived. Training data may include user input, including user data. Machine-learning module may perform determinations, classification, and/or analysis steps, methods, processes, or the like as described in this disclosure using machine learning processes. A "machine learning process," as used in this disclosure, is a process that automatedly uses training data to generate an algorithm that will be performed by a computing device/module to produce outputs given data provided as inputs; this is in contrast to a non-machine learning software program where the commands to be executed are determined in advance by a user and written in a programming language. In one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database, such as any database described in this disclosure. For example, light emission training data inputs may include user data and outputs may include light emission parameters. In other embodiments, machine-learning module may obtain light emission training data by querying a communicatively connected database that includes past inputs and outputs of light emission machine learning model 128. Training data may include inputs from various types of databases, resources, and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Training data may include previous outputs such that the retrained machine-learning module 128 iteratively produces outputs, thus creating a feedback loop. For example, an input may include the user data 120 and an output may include light emission parameters 132. For example, an input may also include diagnostic test data and an output may include light emission parameters as an output. Training data may include previous outputs such that light emission machine learning model 128 iteratively produces outputs. Light emission machine learning model 128 using a machine-learning process may output converted data based on input of training data. In an embodiment, analyzing the user input comprising the plurality of user related data may include determining the plurality of light emission parameters 132 using a machine learning model, such as light emission machine learning model 128 generated by light emission module.

Still referring to FIG. 1, apparatus 100 may be configured to treat a user with the light-emitting device 140 in an oral tissue area. "Oral tissue area" as used in this disclosure is defined as the area within the oral cavity limits. For example, oral tissue area may include pharyngeal and palatal soft tissues. In an embodiment, the patient may be treated with the light-emitting device one time. In an embodiment, the patient may be treated with the light-emitting device a plurality of times. In an embodiment, the patient may be treated with the light-emitting device three or more times. In an embodiment, the patient may be treated with the light-emitting device three times For example, a user may need to guide light-emitting device 140 in the pharyngeal area three times before the tissue/skin is properly destroyed in order to relieve patient of sleep apnea symptoms.

Referring to FIG. 1, user input 116 may include, but is not limited to text input, engagement with icons of a user interface, and the like. Text input may include, without limitation, entry of characters, words, strings, symbols, and the like. In some embodiments, user input 116 may include one or more interactions with one or more elements of a user interface. A "user interface" as used in this disclosure is an interface including set of one or more pictorial and/or graphical icons corresponding to one or more computer actions. User interface may be configured to receive user input 116. User interface may include one or more event handlers. An "event handler" as used in this disclosure is a callback routine that operates asynchronously once an event takes place. Event handlers may include, without limitation, one or more programs to perform one or more actions based on user input, such as generating pop-up windows, submitting forms, changing background colors of a webpage, and the like. Event handlers may be programmed for specific user input, such as, but not limited to, mouse clicks, mouse hovering, touchscreen input, keystrokes, and the like. For instance, and without limitation, an event handler may be programmed to generate a pop-up window if a user double clicks on a specific icon. User input 116 may include, a manipulation of computer icons, such as, but not limited to, clicking, selecting, dragging and dropping, scrolling, and the like. In some embodiments, user input 116 may include an entry of characters and/or symbols in a user input field. A "user input field" as used in this disclosure is a portion of user interface configured to receive data from an individual. A user input field may include, but is not limited to, text boxes, search fields, filtering fields, and the like. In some embodiments, user input 116 may include touch input. Touch input may include, but is not limited to, single taps, double taps, triple taps, long presses, swiping gestures, and the like. In some embodiments, user interface may be displayed on, without limitation, monitors, smartphones, tablets, vehicle displays, and the like. Vehicle displays may include, without limitation, monitors and/or systems in a vehicle such as multimedia centers, digital cockpits, entertainment systems, and the like. One of ordinary skill in the art upon reading this disclosure will appreciate the various ways a user may interact with user interface.

Still referencing FIG. 1, apparatus 100 may be configured to generate a light emission optimization model. In one embodiment, light emission optimization model, may include an optimization criterion. An "optimization criterion," as used in this disclosure, is a value that is sought to be maximized or minimized in a process. For instance, in a non-limiting example, optimization criterion may include any description of a desired value or range of values for one or more attributes of an optimized plurality of light emission parameters; desired value or range of values may include a maximal or minimal value, a range between maximal or minimal values, or an instruction to maximize or minimize an attribute. In a non-limiting example, optimization criterion may specify a range of suitable power density settings. In another non-limiting example, optimization criterion may specify a range of wavelength settings dependent on the patient's tissue/skin thickness needed to prevent skin damage while still targeting specific tissues/skin. In another non-limiting example, optimization criterion may specify one or more tolerances for each range. In yet another non-limiting example, optimization criterion may assign weights to different settings such as the power density settings, the wavelength settings, and the pulse width settings. In some embodiments, light emission optimization model may be formulated as a linear objective function. Light emission optimization model may solve an objective function using a linear program such as without limitation a mixed-integer program. A "linear program," as used in this disclosure, is a program that optimizes a linear objective function, given at least a constraint. For example, at least a constrain may specify that each plurality of light emission parameters 132 is assigned to only one skin type, and each skin type is assigned only one plurality of light emission parameters 132. Plurality of light emission parameters 132 may include any parameters as described above. Plurality of light emission parameters 132 may be optimized for a maximum score combination of all generated skin selections. In an embodiment, a light emission optimization model may determine a combination of different settings for the light-emitting device 140 that maximizes a total score subject to a constraint that all plurality of light emission parameters 132 are paired to exactly one skin type. Not all skin types may receive a plurality of light emission parameters 132 pairing since each user may only receive one plurality of light emission parameters 132.

Still referring to FIG. 1, apparatus 100 may be configured to provide a recommendation of plurality of light emission parameters 132 to a patient and/or to a medical provider, caretaker and the like. In some embodiments, apparatus 100 may receive user feedback regarding the recommendation of plurality of light emission parameters 132 such as prior user experience including burns, side effects, and the like, this information may then be utilized to update the light emission machine learning module 128 training data via a feedback loop. The feedback may be received from a patient survey, questionnaire, doctor's notes and the like. Apparatus 100 may update a recommendation of the plurality of light emission parameters 132 as a function of user feedback. In some embodiments, apparatus 100 may be configured to allow adjustments of percentage of each setting as a function of user feedback, such as a range of power density settings, wavelength settings, and pulse width settings.

Still referring to FIG. 1, apparatus 100 may be configured to compare the plurality of light emission parameters 132 to a safety threshold. A "safety threshold," as described herein, is a quantitative datum or collection of data representing a maximal or minimal value consistent with safe operation of an apparatus 100 and the plurality of light emission parameters 132. Safety threshold may include a single numerical value, a vector or n-tuple of numerical values, and/or any other suitable representation. For example, a safety threshold may include a maximum power density setting that may not be exceeded. Apparatus 100 may be configured to receive a safety threshold as an input.

In an embodiment, apparatus 100 may include a notification system. "Notification system" as used in the disclosure refers to the notification of the user of the apparatus 100 that an event has occurred. For example, the user may be notified when the light-emitting device 140 focuses on an area for too long. The user may also be notified if the light-emitting device 140 has been guided beyond a predetermined area calculated by the plurality of body parameters. "Predetermined area" as used in the disclosure refers to the area the light-emitting device 140 will be guided over. For example, the user may wish to provide light on only one small area of patient's throat and nowhere else in the mouth area. The predetermined area may be calculated by the plurality of boundary parameters. Notification system may be a pop-up screen on a user display, a flashing light on the light-emitting device 140, a sound from a speaker connected to the computer system and the like. Notification system may also be used to notify a user when user has exceeded a repetition threshold. Repetition threshold is the number of repetitions that are calculated by the repetition datum.

In another embodiment, apparatus 100 may include a shutoff switch. A shutoff switch as defined in the disclosure is any switch, push button or similar mechanism that can deactivate the light-emitting device 140. Shutoff switch may also be automatic such that the computer system activates the shutoff switch when an event occurs. For example, shutoff switch may be activated when the repetition threshold has been exceeded by a predetermined amount. An automatic shutoff switch aids in the prevention of burns or unwanted light therapy by the user onto a patient.

In an embodiment, apparatus 100 may include an automated arm. "Automated arm" as described in the disclosure refers to a mechanical arm capable of movement along a predetermined area. Automated arm may be attached to the laser-emitting device and used to guide the laser emitting device along a predetermined area. Automated arm removes the need for a user to manually control the light-emitting device 140. Instead, automated arm may be controlled using the computer system. As described above, apparatus 100 may utilize machine learning to guide the automated arm along a predetermined area. The boundary datum may be used to guide the arm within a designated area. Automated arm may be utilized in a similar fashion to a computer controlled cutting tool.

Figure 2:
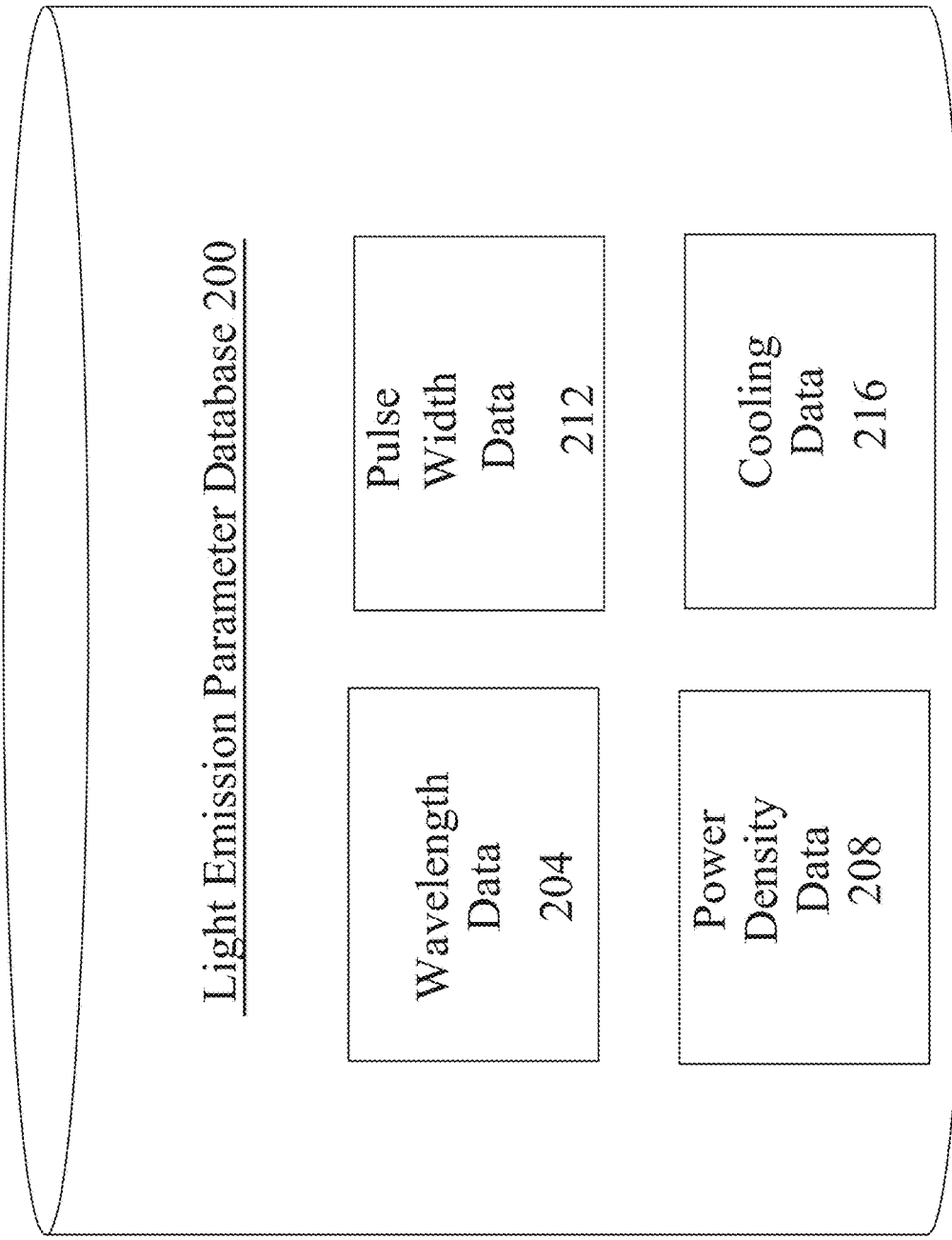
FIG. 2 is an exemplary embodiment of a database of light emission parameter data.

Now referencing FIG. 2, an illustration of an exemplary embodiment of a light emission parameter database 200 is presented. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 2, in some embodiments, database 200 may include wavelength parameter data 204. Wavelength parameter data may include a setting of light-emitting device 140 which may range from 400 nanometers to 12000 nanometers. Wavelength setting of the light-emitting device 140 may be controlled through a dial or through input device as described above. The data correlating to a specific wavelength setting may be quantified as wavelength datum. Database 200 may also include power density data 208. Power density data 208 may include a power density setting which is calculated as a function of a power and a spot size of the light-emitting device. Power of the light-emitting device is power that is delivered through the light emitted from the light-emitting device and the like. Database 200 may also include pulse width data 212. Pulse width data 212 may include the exposure time of the light-emitting device 140 on the surface of a patient's skin. Pulse width may be quantified in seconds. The duration of the pulse width may be dependent on the thickness of user's tissue/skin and the like. Database 200 may also include colling data 216. Cooling data 216 may include any form of cooling that may occur to reduce the temperature on a surface. For example, light-emitting device 140 may contain a fan that blows air onto the heated surface, thereby dissipating any heat. Any and all determinations described above may be performed and analyzed using an optimization program.

Figure 3:
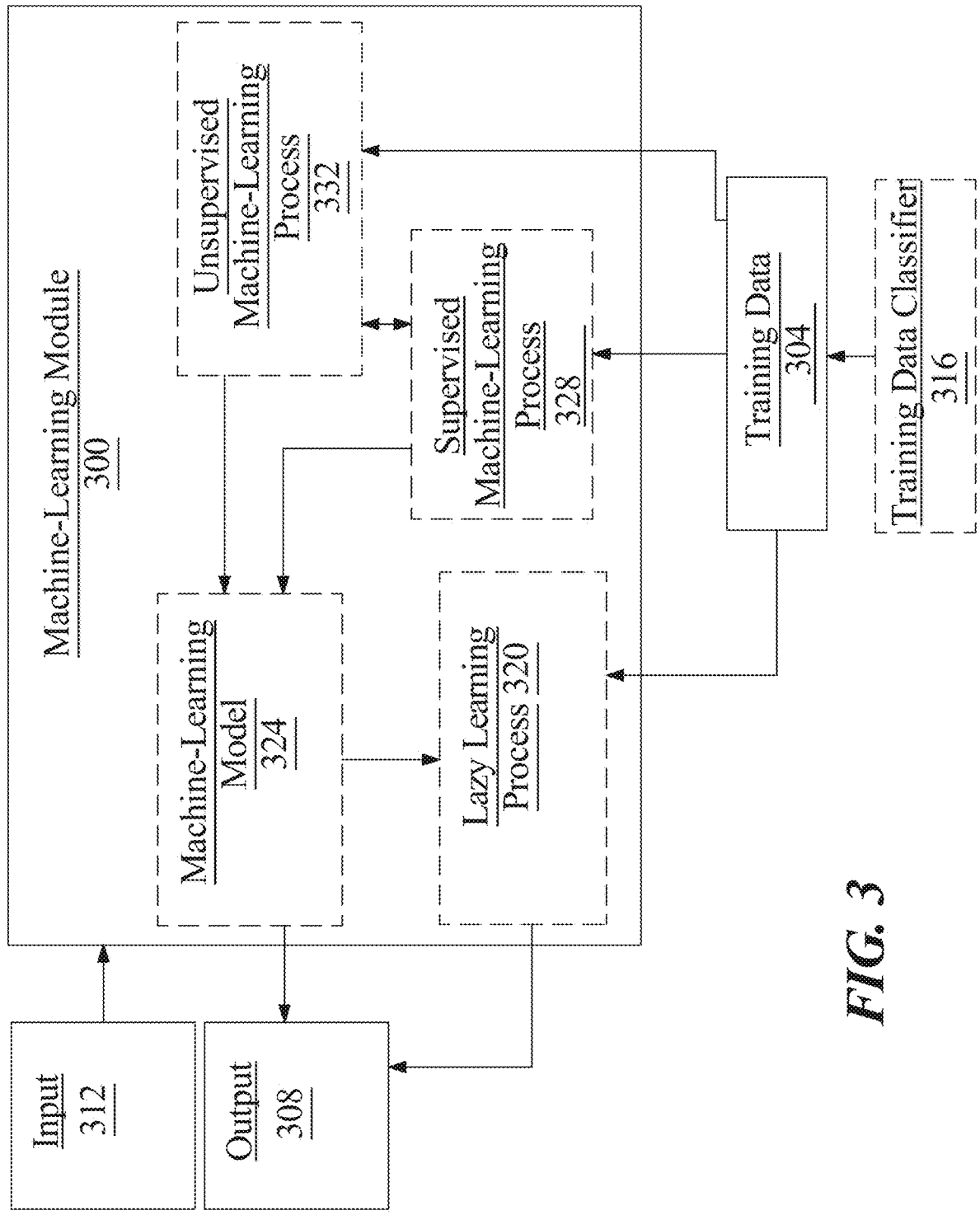
FIG. 3 is a diagram of an exemplary embodiment of a machine-learning module.

Referring now to FIG. 3, a diagram of an exemplary embodiment of a machine-learning module is presented. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 4:
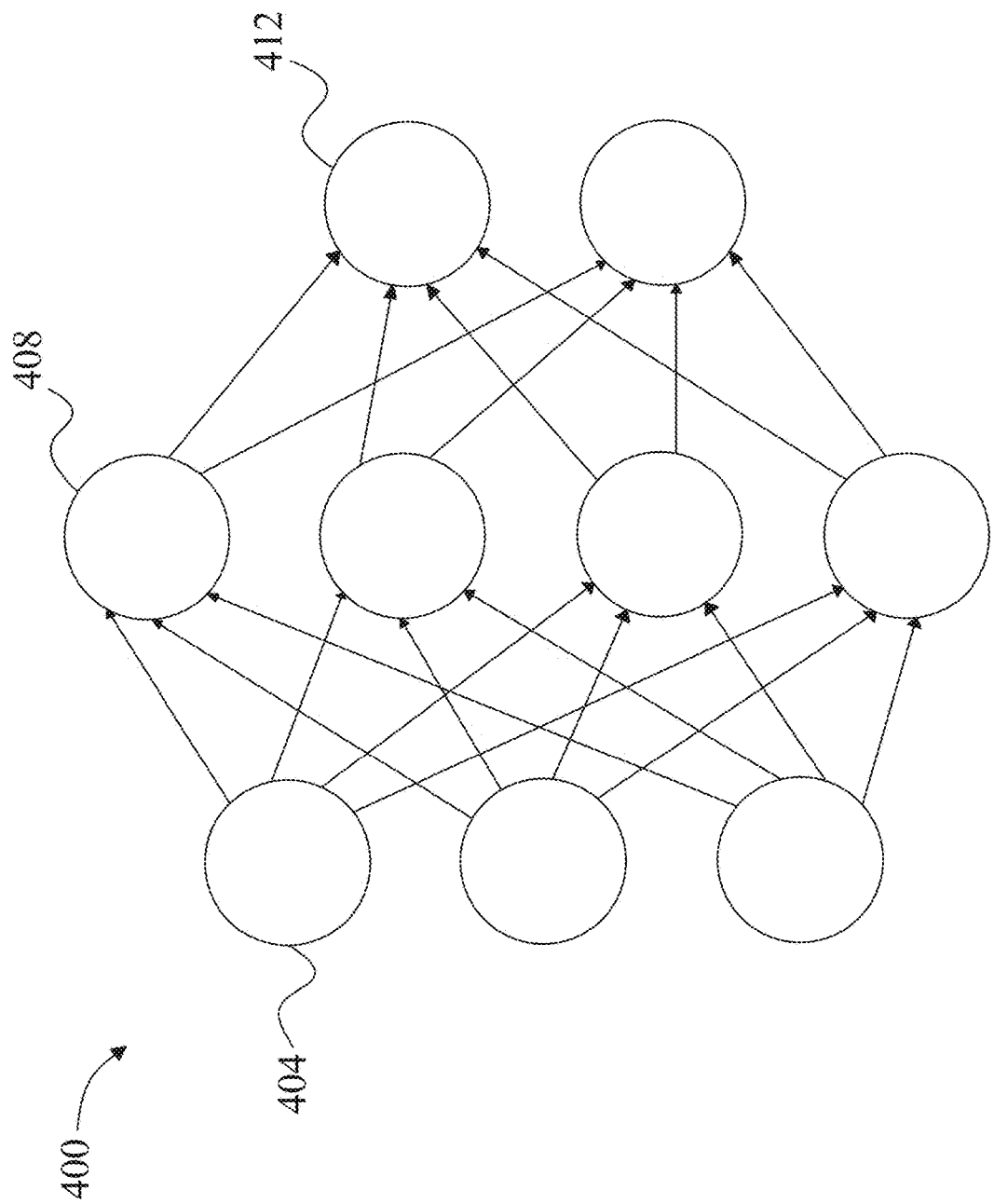
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
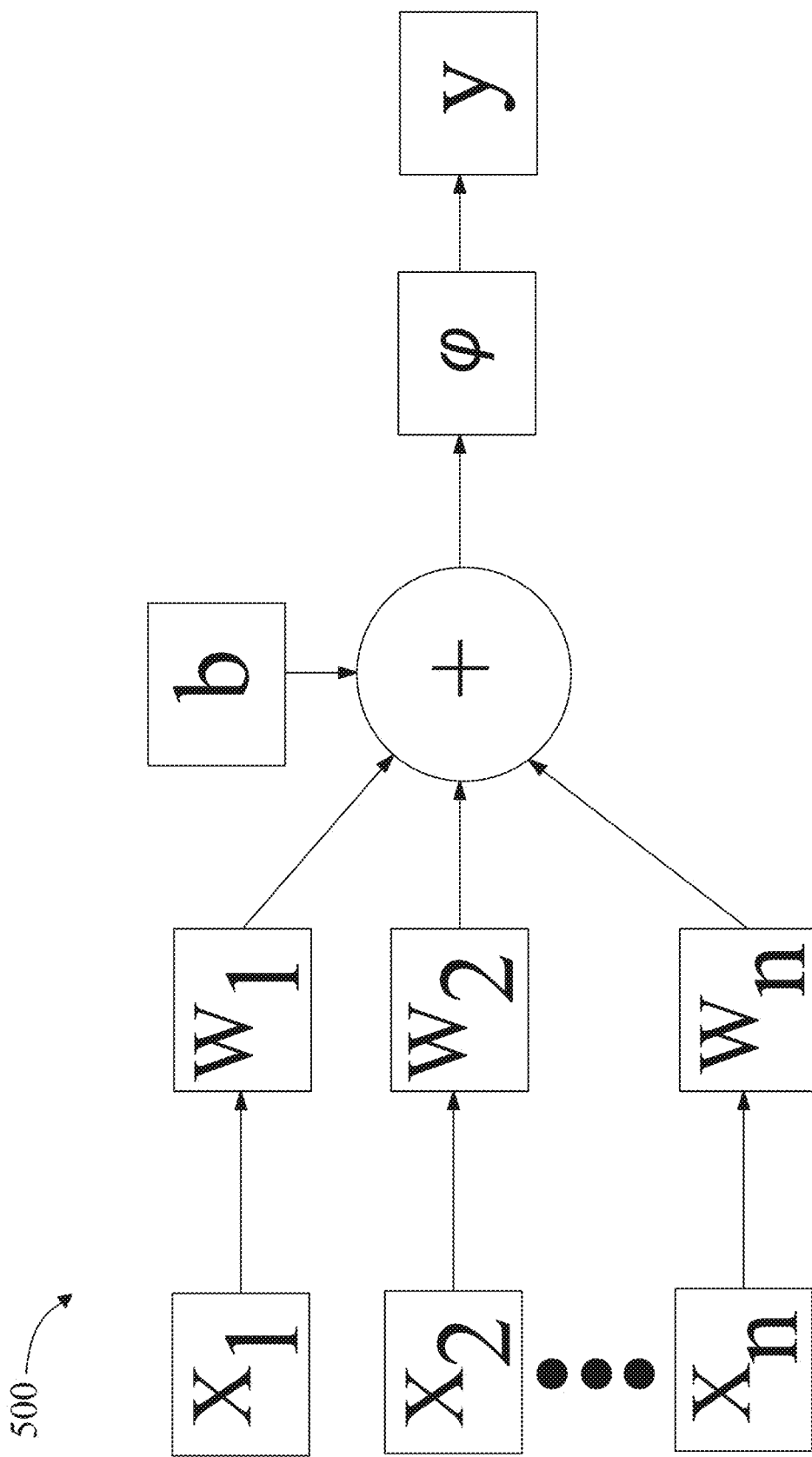
FIG. 5 is a diagram of an exemplary embodiment of a node of a neural network.

Referring now to FIG. 5, an exemplary embodiment 500 of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
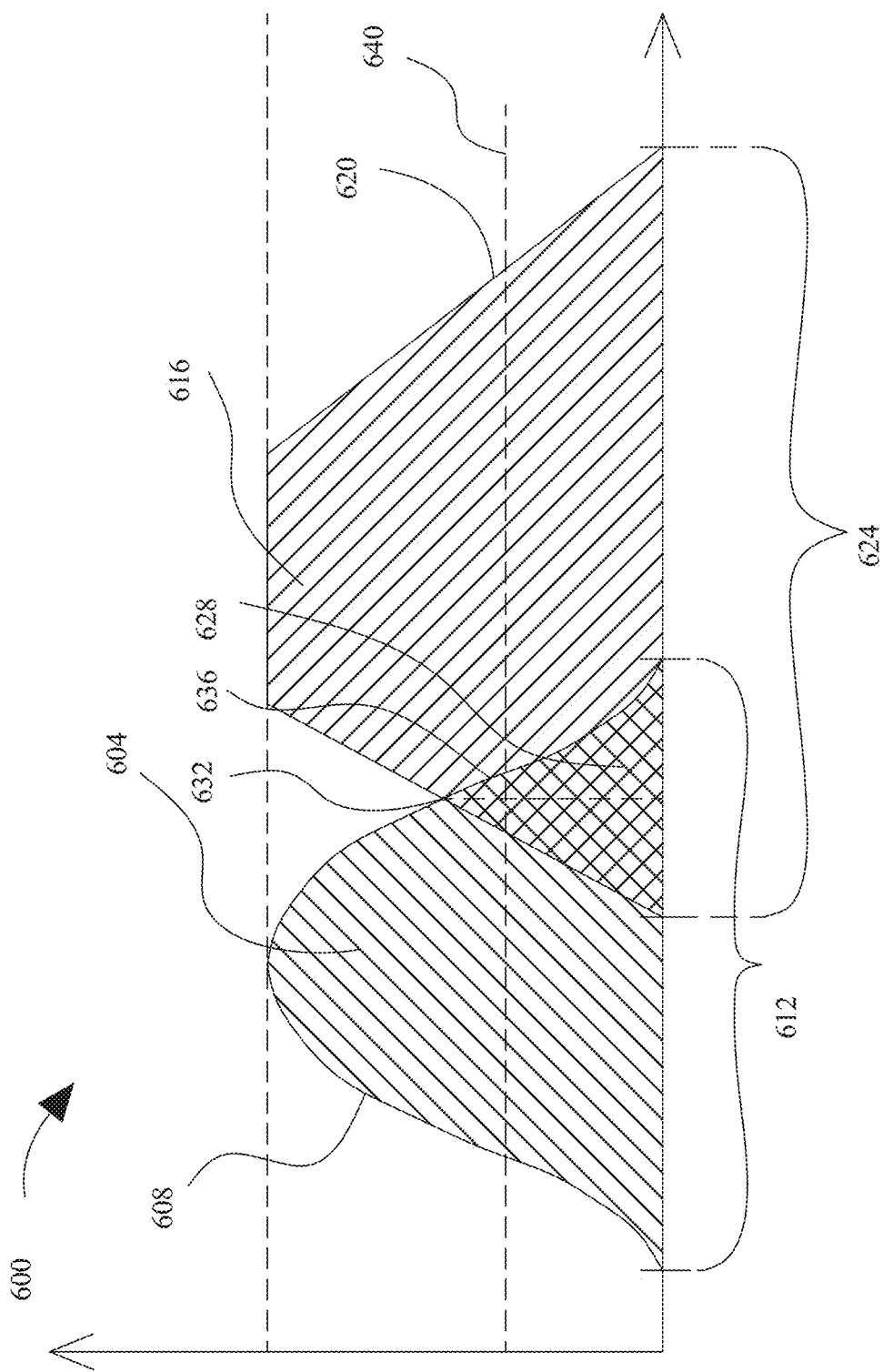
FIG. 6 is a diagram of an exemplary embodiment of a fuzzy set comparison.

Referring now to FIG. 6, an aggregate plurality of light emission parameters 132 may be created using a fuzzy inference system, where the degrees of match are represented by fuzzy sets, and inferencing rules propagate degrees of match to output fuzzy sets and/or scores, an exemplary embodiment of fuzzy set comparison 600 is illustrated. Referring to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 308 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 6, first fuzzy set 604 may represent any value or combination of values as described above, including output from one or more machine-learning models and the plurality of light emission parameters. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, threshold may indicate a sufficient degree of overlap between an output from one or more machine-learning models and/or plurality of light emission parameters and a predetermined class, such as without limitation a light emission categorization, for combination to occur as described above. Alternatively or additionally, each threshold may be tuned by a machine-learning and/or statistical process, for instance and without limitation as described in further detail below.

Further referring to FIG. 6, in an embodiment, a degree of match between fuzzy sets may be used to classify a plurality of user data with plurality of light emission parameters. For instance, if a plurality of light emission parameters has a fuzzy set matching plurality of user data fuzzy set by having a degree of overlap exceeding a threshold, computing device may classify the plurality of user data as belonging to the plurality of light emission parameters categorization. Where multiple fuzzy matches are performed, degrees of match for each respective fuzzy set may be computed and aggregated through, for instance, addition, averaging, or the like, to determine an overall degree of match.

Still referring to FIG. 6, in an embodiment, a plurality of user data may be compared to multiple plurality of light emission parameters categorization fuzzy sets. For instance, plurality of user data may be represented by a fuzzy set that is compared to each of the multiple plurality of light emission parameters categorization fuzzy sets; and a degree of overlap exceeding a threshold between the plurality of user data fuzzy set and any of the multiple plurality of light emission parameters categorization fuzzy sets may cause computing device o classify the plurality of user data as belonging to plurality of light emission parameters categorization. For instance, in one embodiment there may be two plurality of light emission parameters categorization fuzzy sets, representing respectively plurality of light emission parameters categorization and a plurality of light emission parameters categorization. First plurality of light emission parameters categorization may have a first fuzzy set; second plurality of light emission parameters categorization may have a second fuzzy set; and plurality of user data may have a plurality of user data fuzzy set. Computing device, for example, may compare a plurality of user data fuzzy set with each of plurality of light emission parameters categorization fuzzy set and in plurality of light emission parameters categorization fuzzy set, as described above, and classify a plurality of user data to either, both, or neither of plurality of light emission parameters categorization or in the plurality of light emission parameters categorization. Machine-learning methods as described throughout may, in a non-limiting example, generate coefficients used in fuzzy set equations as described above, such as without limitation x, c, and σ of a Gaussian set as described above, as outputs of machine-learning methods.

Still referring to FIG. 6, a computing device may use a logic comparison program, such as, but not limited to, a fuzzy logic model to determine a plurality of light emission parameters response. An plurality of light emission parameters response may include, but is not limited to, similar, not similar and the like; each such plurality of light emission parameters response may be represented as a value for a linguistic variable representing plurality of light emission parameters response or in other words a fuzzy set as described above that corresponds to a degree of as calculated using any statistical, machine-learning, or other method that may occur to a person skilled in the art upon reviewing the entirety of this disclosure. In other words, a given element of plurality of user data may have a first non-zero value for membership in a first linguistic variable and a second non-zero value for membership in a second linguistic variable value. In some embodiments, determining a plurality of light emission parameters categorization may include using a linear regression model. A linear regression model may include a machine learning model. A linear regression model may be configured to map data of plurality of user data, such as degree of compatibility to one or more plurality of light emission parameters considerations. A linear regression model may be trained using a machine learning process. A linear regression model may map statistics such as, but not limited to, quality of plurality of user data compatibility. In some embodiments, determining plurality of light emission parameters of plurality of user data may include using a plurality of light emission parameters classification model. A plurality of light emission parameters classification model may be configured to input collected data and cluster data to a centroid based on, but not limited to, frequency of appearance, linguistic indicators of quality, and the like. Centroids may include scores assigned to them such that quality of compatibility of plurality of user data may each be assigned a score. In some embodiments plurality of light emission parameters classification model may include a K-means clustering model. In some embodiments, plurality of light emission parameters classification model may include a particle swarm optimization model. In some embodiments, determining the plurality of light emission parameters of a plurality of user data may include using a fuzzy inference engine. A fuzzy inference engine may be configured to map one or more plurality of user data record elements using fuzzy logic. In some embodiments, plurality of user data may be arranged by a logic comparison program into plurality of light emission parameters arrangement. An "plurality of light emission parameters arrangement" as used in this disclosure is any grouping of objects and/or data based on skill level and/or output score. This step may be implemented as described above in FIGS. 1-2. Membership function coefficients and/or constants as described above may be tuned according to classification and/or clustering algorithms. For instance, and without limitation, a clustering algorithm may determine a Gaussian or other distribution of questions about a centroid corresponding to a given compatibility level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 6, an inference engine may be implemented according to input and/or output membership functions and/or linguistic variables. For instance, a first linguistic variable may represent a first measurable value pertaining to plurality of user data, such as a degree of compatibility of an element, while a second membership function may indicate a degree of in plurality of light emission parameters of a subject thereof, or another measurable value pertaining to plurality of user data. Continuing the example, an output linguistic variable may represent, without limitation, a score value. An inference engine may combine rules. The degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a,⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 6, plurality of user data to be used may be selected by user selection, and/or by selection of a distribution of output scores, such as 60% match, 40% moderate match, and 0% no match or the like. Each plurality of light emission parameters categorization may be selected using an additional function such as in plurality of light emission parameters as described above.

Figure 7:
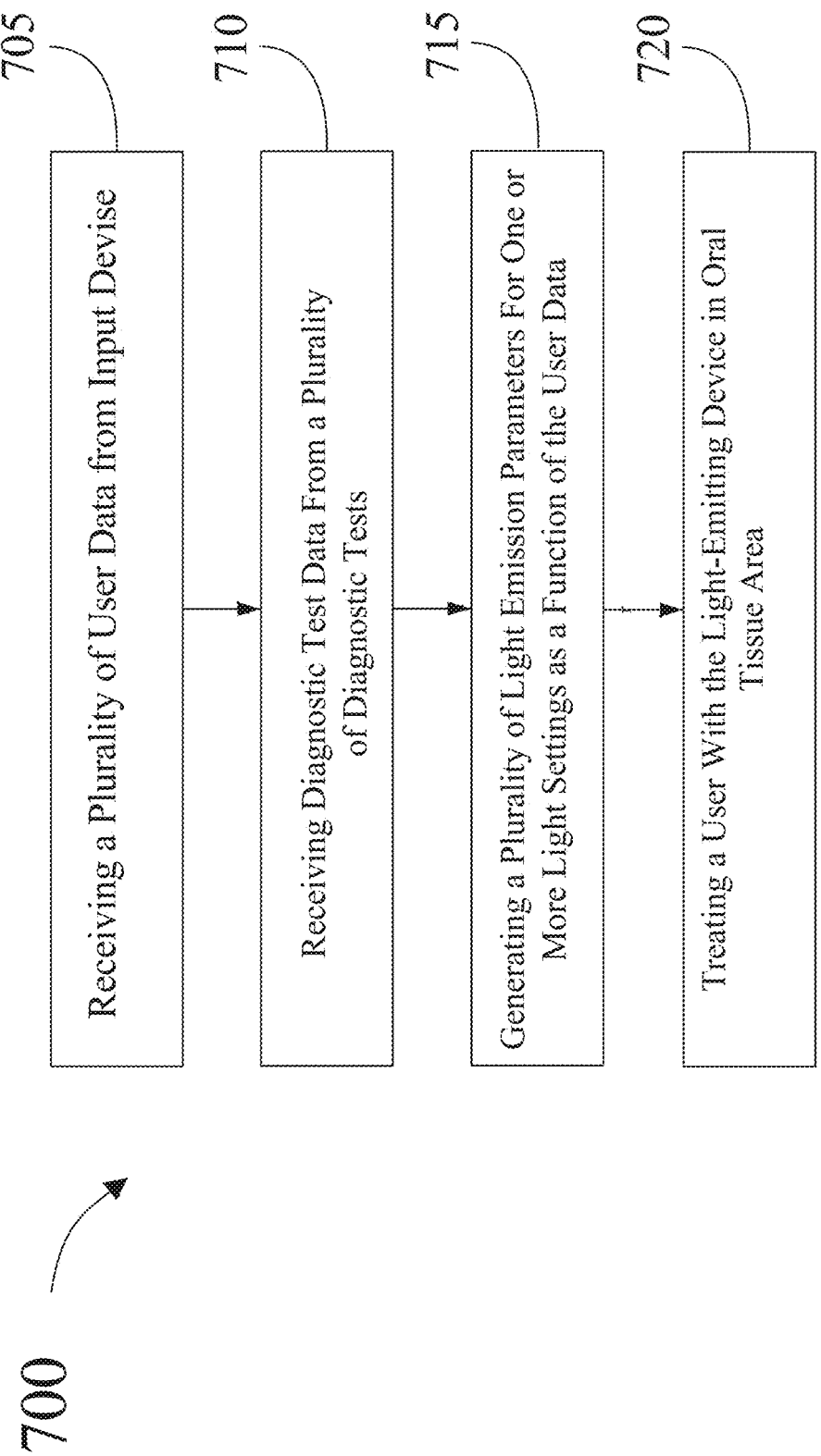
FIG. 7 is a flowchart of a method of a method for a sleep disorder treatment.

Referring now to FIG. 7, a method 700 of using an apparatus for a sleep disorder treatment is illustrated. At step

705, method 700 includes receiving a plurality of user data 120. User data 120 may be received through user input, from external computing devices, such as a remote device, and the like. This step may be implemented as described above in FIGS. 1-6, without limitation.

Still referring to FIG. 7, at step 710, method 700 includes receiving diagnostic test data 124 from a plurality of diagnostic tests. The plurality of diagnostic tests may include a nocturnal polysomnography test. The diagnostic test data may include blood count test data, skin data, collagen data and a boundary datum. This step may be implemented as described above in FIGS. 1-6, without limitation.

Still referring to FIG. 7, at step 715, method 700 includes generating a plurality of light emission parameters for one or more light settings as a function of the user data 120. The at least one light setting of the light-emitting device further includes a generation of a wavelength setting. Generating the plurality of light emission parameters includes generating the light emission parameter as a function of the skin datum and a light emission machine learning model. The plurality of light emission parameters further includes receiving the plurality of user data from the input device, training the light emission learning model as a function of a training datum and generating the plurality of light emission parameters as a function of the skin datum and the light emission machine learning model. This step may be implemented as described above in FIGS. 1-6, without limitation.

Still referring to FIG. 7, at step 720, method 700 includes treating a user with the light-emitting device in the oral tissue area. The user may be treated with the light-emitting device in the oral tissue area at least three times. This step may be implemented as described above in FIGS. 1-6, without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
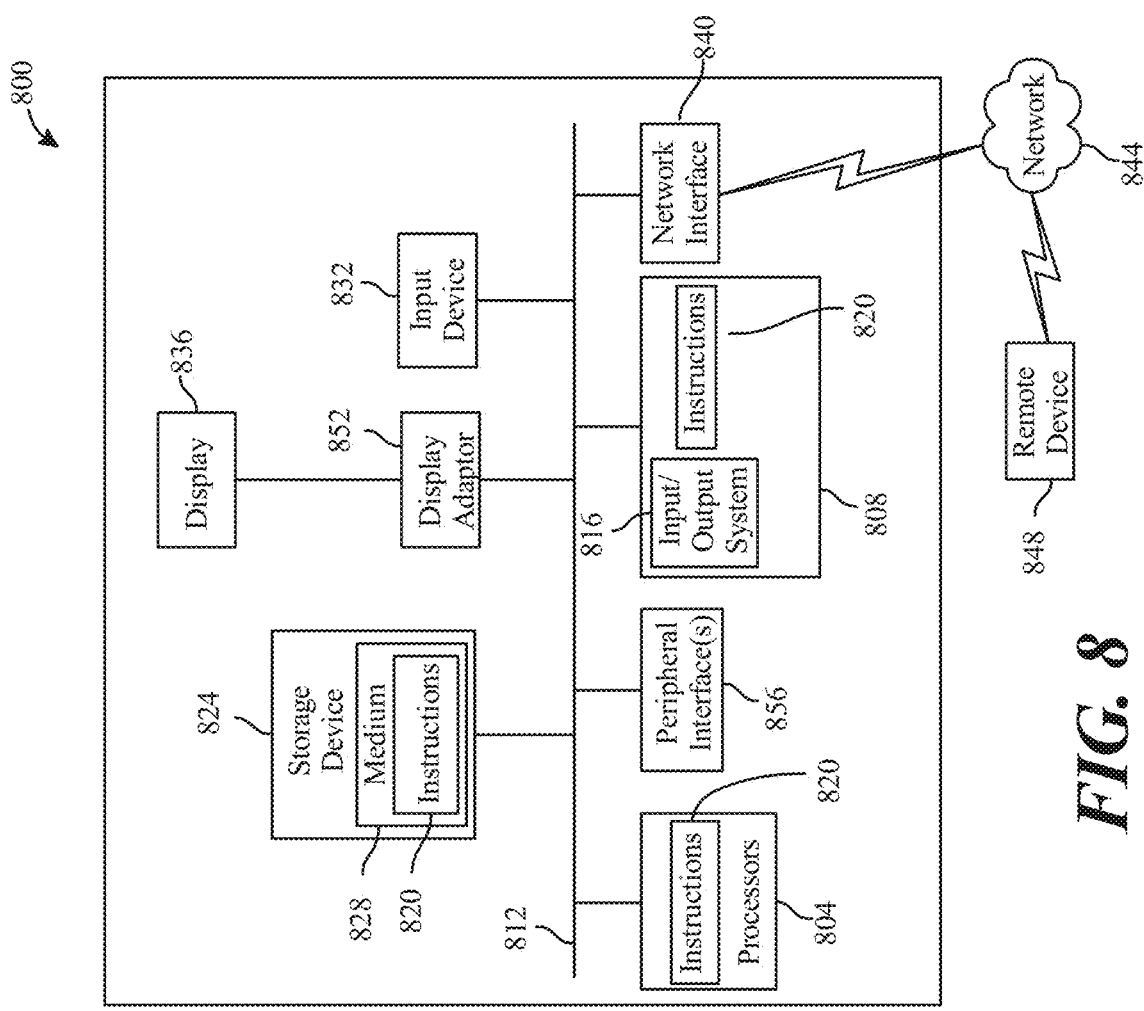
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components hereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light-emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for a sleep disorder treatment, the apparatus comprising:
   an input device;
   a light-emitting device, comprising one or more light settings;
   a processor; and
   a memory communicatively connected to the processor, the memory containing instructions configuring the processor to:
   receive user data from the input device;
   receive diagnostic test data from a plurality of diagnostic tests, wherein a diagnostic test comprises a nocturnal polysomnography test and at least an autoimmune test;
   generate a plurality of light emission parameters for the one or more light settings as a function of the user data; and
   treat a user with the light-emitting device in an oral tissue area.

2. The apparatus of claim 1, wherein the input device includes at least one photoelectric sensor, and the memory contains instructions configuring the processor to receive user data from the at least one photoelectric sensor.

3. The apparatus of claim 1, wherein the diagnostic test data comprises blood count test data.

4. The apparatus of claim 1, wherein the plurality of user data of the input device further comprises a tissue datum.

5. The apparatus of claim 1, wherein the plurality of user data of the input device further comprises a collagen datum.

6. The apparatus of claim 1, wherein the plurality of user data from the input device further comprises a boundary datum.

7. The apparatus of claim 1 wherein treating the user with the light-emitting device comprises treating the user with the light-emitting device at least three times.

8. The apparatus of claim 1, wherein generating the plurality of light emission parameters for the one or more light settings comprises generating a wavelength setting.

9. The apparatus of claim 1, wherein generating the plurality of light emission parameters further comprises generating the plurality of light emission parameter as a function of a skin datum and a light emission machine learning model.

10. The apparatus of claim 9, the plurality of light emission parameters further comprising:
   receiving the plurality of user data from the input device;
   training the light emission machine learning model as a function of light emission training data; and
   generating the plurality of light emission parameters as a function of the skin datum and the light emission machine learning model.

11. A method for a sleep disorder treatment comprising:
   a light-emitting device comprising one or more light settings;
   receiving, by a processor, a user data from an input device;
   receiving, by the processor, diagnostic test data from a plurality of diagnostic tests, wherein a diagnostic test comprises a nocturnal polysomnography test and at least an autoimmune test;
   generating, by the processor, a plurality of light emission parameters for one or more light settings as a function of the user data; and
   treating a user with the light-emitting device in an oral tissue area.

12. The method of claim 11, wherein the input device includes at least one photoelectric sensor, and the memory contains instructions configuring the processor to receive data from the at least one photoelectric sensor.

13. The method of claim 11, wherein the diagnostic test data comprises blood count test data.

14. The method of claim 11, wherein the plurality of user data of the input device further comprises a skin datum.

15. The method of claim 11, the plurality of data of the input device further comprising a collagen datum.

16. The method of claim 11, wherein the plurality of user data from the input device further comprises a boundary datum.

17. The method of claim 11 wherein treating the user with the light-emitting device comprises treating the user with the light-emitting device at least three times.

18. The method of claim 11, wherein generating the plurality of light emission parameters for the one or more light settings comprises generating a wavelength setting.

19. The method of claim 11, wherein generating the plurality of light emission parameters further comprises generating the light emission parameter as a function of the skin datum and a light emission machine learning model.

20. The method of claim 19, the plurality of light emission parameters further comprising:
   receiving the plurality of user data from the input device;
   training the light emission learning model as a function of a training datum; and
   generating the plurality of light emission parameters as a function of the skin datum and the light emission machine learning model.

\* \* \* \* \*